(12) United States Patent
Akkermans et al.

(10) Patent No.: US 8,187,202 B2
(45) Date of Patent: May 29, 2012

(54) METHOD AND APPARATUS FOR ACOUSTICAL OUTER EAR CHARACTERIZATION

(75) Inventors: Antonius Hermanus Maria Akkermans, Eindhoven (NL); Alphons Antonius Maria Lambertus Bruekers, Eindhoven (NL); Vincent Van Der Leest, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1048 days.

(21) Appl. No.: 12/067,305

(22) PCT Filed: Sep. 13, 2006

(86) PCT No.: PCT/IB2006/053252
§ 371 (c)(1),
(2), (4) Date: Mar. 19, 2008

(87) PCT Pub. No.: WO2007/034371
PCT Pub. Date: Mar. 29, 2007

(65) Prior Publication Data
US 2008/0262382 A1    Oct. 23, 2008

(30) Foreign Application Priority Data
Sep. 22, 2005  (EP) .................................... 05108781

(51) Int. Cl.
*A61B 5/00*  (2006.01)
(52) U.S. Cl. ........................................ 600/559; 382/115
(58) Field of Classification Search .................. 600/559; 382/115
See application file for complete search history.

(56) References Cited

U.S. PATENT DOCUMENTS

| 5,787,187 | A | 7/1998 | Bouchard et al. |
| 7,529,379 | B2* | 5/2009 | Zurek et al. ................. 381/328 |
| 2002/0057805 | A1* | 5/2002 | Kato et al. ..................... 381/56 |
| 2004/0215968 | A1 | 10/2004 | Rodwell et al. |
| 2004/0218788 | A1* | 11/2004 | Geng ........................... 382/118 |

FOREIGN PATENT DOCUMENTS

| EP | 1205884 A2 | 5/2002 |
| GB | 2375205 A | 11/2002 |
| JP | 2002165778 A | 6/2002 |

OTHER PUBLICATIONS

Chris A. Lanciani: Auditory Perception and the MPEG Audio Standard, Georgia Institute of Tech. Aug. 11, 1995, pp. 1-35.
Pim Tuyls, et al: Anonymous Biometrics: Privacy Protection of Biomertic Templates, Philips Research Eindhoven, The Netherlands, Jul. 11, 2005, slides 28-31.
Akkermans et al: "Acoustic Ear Recognition"; Advances in Biometrics Lecture Notes in Computer Science; LNCS, Springer, Berlin, DE, vol. 3832, pp. 697-705, Dec. 9, 2005.

* cited by examiner

*Primary Examiner* — Max Hindenburg
*Assistant Examiner* — Renee Danega
(74) *Attorney, Agent, or Firm* — Larry Liberchuk

(57) ABSTRACT

The present invention relates to a method and apparatus for characterizing acoustical properties of an outer ear 130, the method comprising the steps of: transmitting a first acoustic signal 125 towards the outer ear 130, receiving a second acoustic signal 150 from the outer ear 130, and characterizing acoustical properties 165 of the outer ear on the basis of the second acoustic signal 150. The method is characterized in that the first acoustic signal 125 comprises at least one of the following elements: music, and speech. The present invention further relates to a method and apparatus for enrolling, authenticating and identifying a person on the basis of acoustical properties of an outer ear 130.

17 Claims, 9 Drawing Sheets

METHOD AND APPARATUS FOR ACOUSTICAL OUTER EAR CHARACTERIZATION

Figure 1:
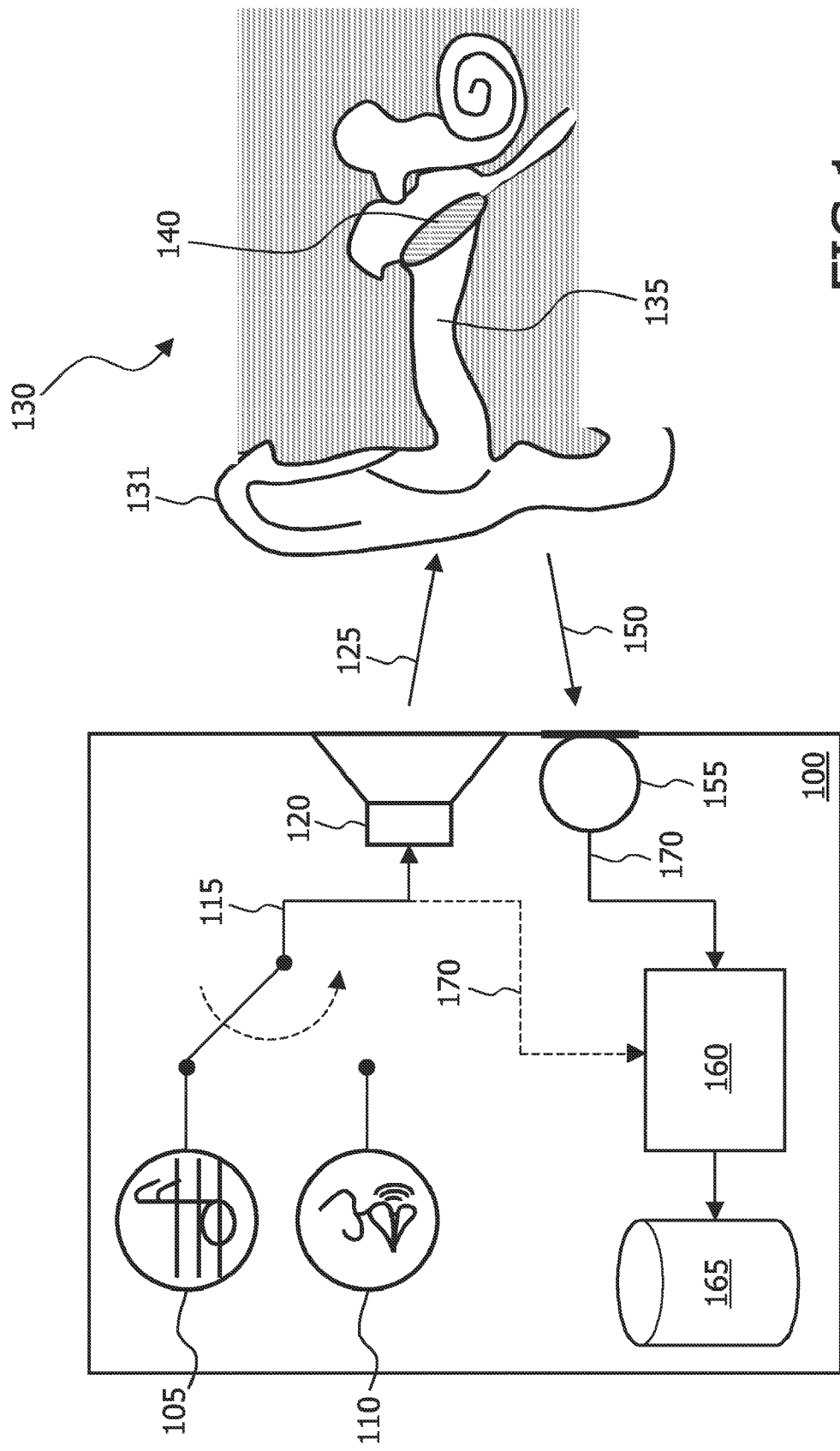

The invention relates to a method of characterizing acoustical properties of an outer ear, the method comprising the steps of: transmitting a first acoustic signal towards the outer ear, receiving a second acoustic signal from the outer ear, and characterizing acoustical properties of the outer ear on the basis of the second acoustic signal. The invention further relates to an apparatus and a system for characterizing acoustical properties of an outer ear, the apparatus and the system each comprising: transmitting means arranged to transmit a first acoustic signal towards the outer ear, receiving means arranged to receive a second acoustic signal from the outer ear, and characterizing means arranged to characterize the acoustical properties of the outer ear on the basis of the second acoustic signal.

In security applications, as well as in every day life, authentication and identification of persons are of paramount importance. Credit cards, ID cards, passports, and badges are used by many people on a daily basis but are stolen and abused quite frequently. As a result, there is a strong drive to develop reliable biometrics that can be acquired in a preferably non-intrusive and convenient manner. However, certain biometrics such as fingerprints have a disadvantage in that they are left involuntarily by their owners and, as a result, malicious parties have successfully forged fingerprints, e.g. using gummy fingers.

The drive for new biometrics has led to the use of acoustical properties of the outer ear as a biometric. U.S. Pat. No. 5,787,187 discloses a system for verifying/recognizing the identity of an individual by characterizing the acoustical properties of the ear canal as a biometric. To this end, a source signal is emitted into the ear canal that comprises e.g. broadband noise, or frequency tones. However, individuals whose outer ear acoustics are being characterized perceive such source signals as intrusive and/or unpleasant.

According to a first aspect of the invention, it is an object to provide a method of acoustical outer ear characterization that is less intrusive for the person being characterized.

This objective is realized in that the method as set forth in the opening paragraph is further characterized in that the first acoustic signal comprises at least one of the following elements: music, and speech.

The advantage of using music or speech for characterizing the outer ear is that a person being characterized will find the characterization process less intrusive than when being confronted with (white) noise, or tone sequences. The present method has the further advantage that it can be conducted during a conversation, or when a person is listening to a message and/or music. The method is so inconspicuous that characterization can take place without the person being aware of it.

When transmitting the first acoustic signal comprising music and/or speech towards the human outer ear, part of the signal will be reflected by the pinna (the visible part of the outer ear), the ear canal, and the eardrum. A second acoustic signal is captured by using a microphone, which signal comprises part of the reflected signal that in turn comprises information with respect to the outer ear structure. The second acoustic signal is used to characterize acoustical properties of the outer ear.

In a first embodiment, the amplitude of the spectral components present in the second acoustic signal is established in order to characterize acoustical properties. In an alternative embodiment, a transfer function is established on the basis of the frequency domain representation of both the source representation and the received second acoustic signal in order to characterize acoustical properties.

The use of music and/or speech allows the use of low-cost consumer electronics loudspeakers and microphones for characterization.

According to a second aspect of the invention, the method of characterizing acoustical properties of an outer ear can be further enhanced by the addition of noise to the music and/or speech used in the characterization process. The added noise may comprise white or colored noise. Although music and/or speech allow characterization, music and/or speech may not comprise all relevant spectral components in the audible spectrum.

Reliability can be improved by adding noise comprising at least the relevant missing spectral components. Furthermore, by using a relatively low amplitude noise signal, in comparison with that of music and/or speech, the less intrusive nature of music and/or speech can be preserved.

According to a third aspect of the invention, the method of characterizing acoustical properties of an outer ear can be further enhanced by using a particularly elegant method of adding noise. The human auditory system is a very sensitive system that can pick up even minute quantities of noise, provided it is quiet. However, in the presence of music and/or speech, the distinguishing capabilities of the human auditory system are compromised.

By exploiting a technique referred to as spectral and temporal masking, it is possible to add noise to an audio signal without a person noticing. More information related to perceptual coding can be found, inter alia, in "Auditory Perception and the MPEG Audio Standard", by Chris A. Lanciani, published by the Georgia Institute of Technology, Aug. 11, 1995, herein incorporated by reference.

The psycho-acoustic model of the human auditory system is used elaborately in lossy digital audio compression techniques. These techniques exploit, inter alia, the fact that the human ear has difficulty in distinguishing small amplitude frequency components in the presence of a, spectrally proximate, frequency component with a substantially larger amplitude. As a result, it is possible to use a coarser quantization for the smaller components, or discard the smaller components altogether in order to reduce the size of the audio representation.

In the above example, the "compressed" signal is distorted; the quantization errors, and/or discarded frequency components can be considered as noise that is added to the original signal. The present invention suggests adding noise based on the psycho-acoustic model of the human auditory system in order to exploit the temporal and/or spectral masking effect, and not to compress the resulting signal but add inaudible noise in order to shape the frequency spectrum of the signal so as to improve characterization of the outer ear.

Methods according to all of these aspects of the invention can be used in systems for biometric authentication or identification of a user that use acoustical properties of the outer ear as a biometric. Usually, two phases can be distinguished in systems for biometric authentication and identification;

an enrolment phase during which reference data is acquired, and an authentication/identification phase during which authentication/identification data is acquired and compared with previously enrolled reference data.

During both phases, the acoustical properties of an outer ear are characterized. As a result, the present invention can be used beneficially in methods for biometric enrolment, authentication, and identification that use acoustical properties of the outer ear as a biometric.

According to a further aspect of the invention, it is an object to provide an apparatus for acoustical outer ear characterization that is less intrusive for the person being characterized.

This objective is realized in that the apparatus as set forth in the opening paragraph is further characterized in that the first acoustic signal comprises at least one of the following elements: music, and speech.

In one embodiment, an apparatus according to the present invention comprises a noise generation means that allows the addition of noise to the first acoustic signal comprising music and/or speech. In an alternative embodiment, the noise generation means is used in combination with a noise generation control means that allows the addition of noise based on a psycho-acoustic model of the human auditory system.

The invention further relates to a device for enrolling the acoustical properties of an outer ear of a person that characterizes acoustical properties according to the present invention, as well as to an apparatus for authenticating and an apparatus for identifying a person using acoustical properties characterized according to the present invention.

According to a further aspect of the invention, it is an object to provide a system for acoustical outer ear characterization that is less intrusive for the person being characterized.

This objective is realized in that the system as set forth in the opening paragraph is further characterized in that the first acoustic signal comprises at least one of the following elements: music, and speech.

The present invention further relates to a telecommunication system configured to provide telecommunication services via a network and remotely authenticate a person. The system comprises two terminals, a first terminal associated with a party, and a second terminal operated by a person. The system is arranged in such a way that, according to the present invention, the two terminals jointly characterize the acoustical properties of the outer ear of the person, wherein the characterized acoustical properties are used by an authentication means comprised in the first terminal that matches the characterized acoustical properties of the outer ear of the person with enrolled acoustical ear properties in order to authenticate the person to said party.

Figure 2:
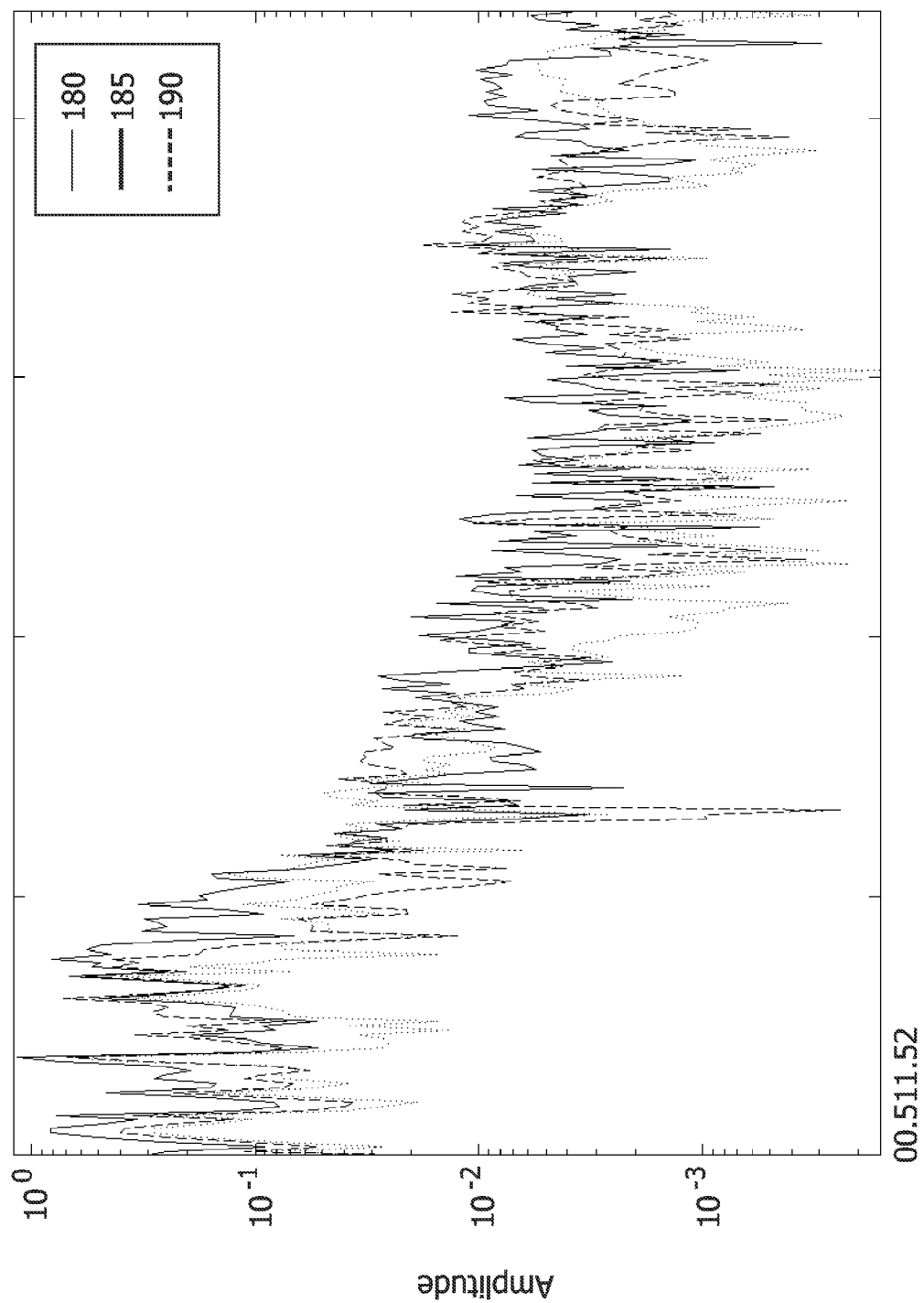
Figure 3:
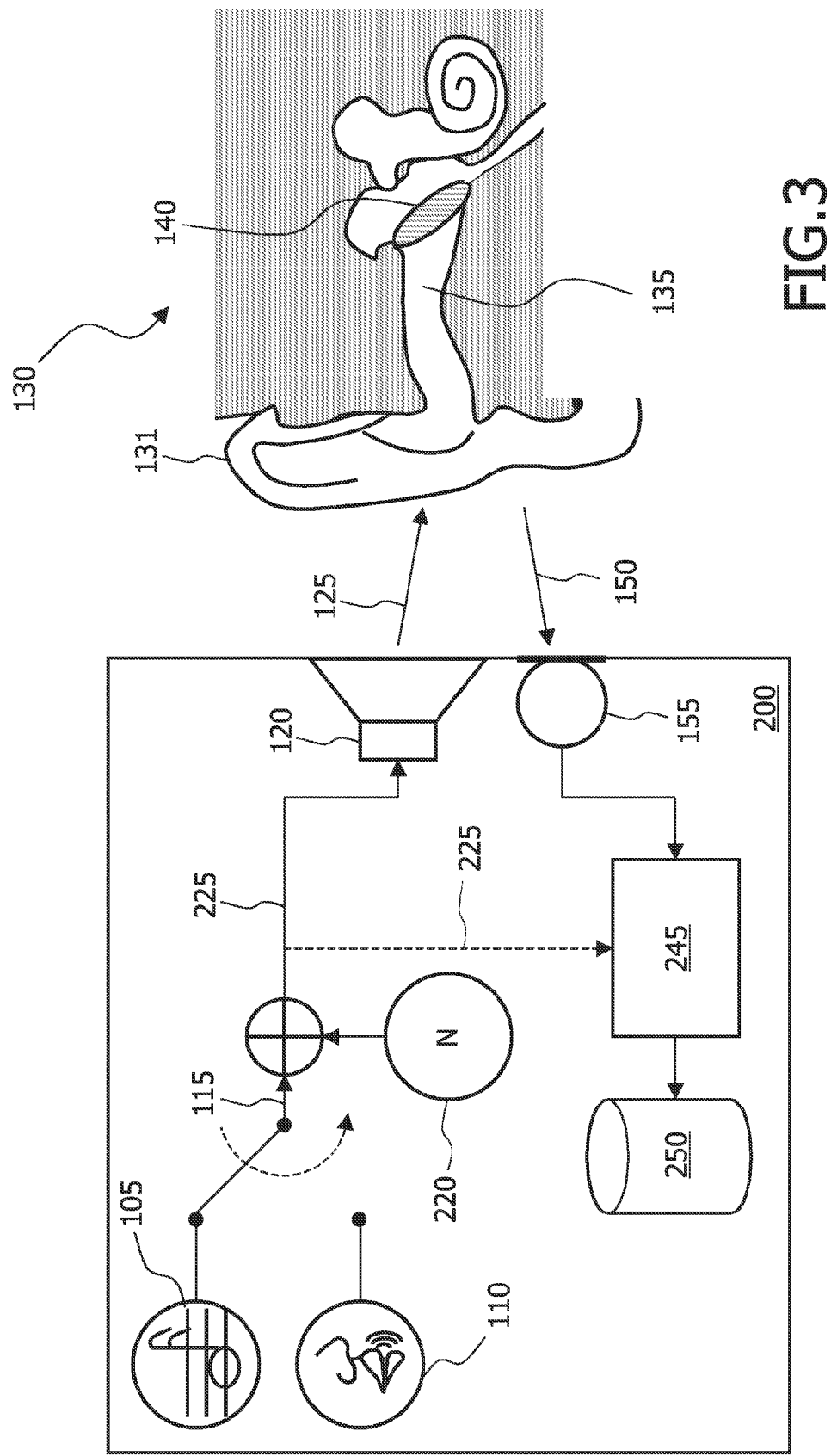
Figure 4:
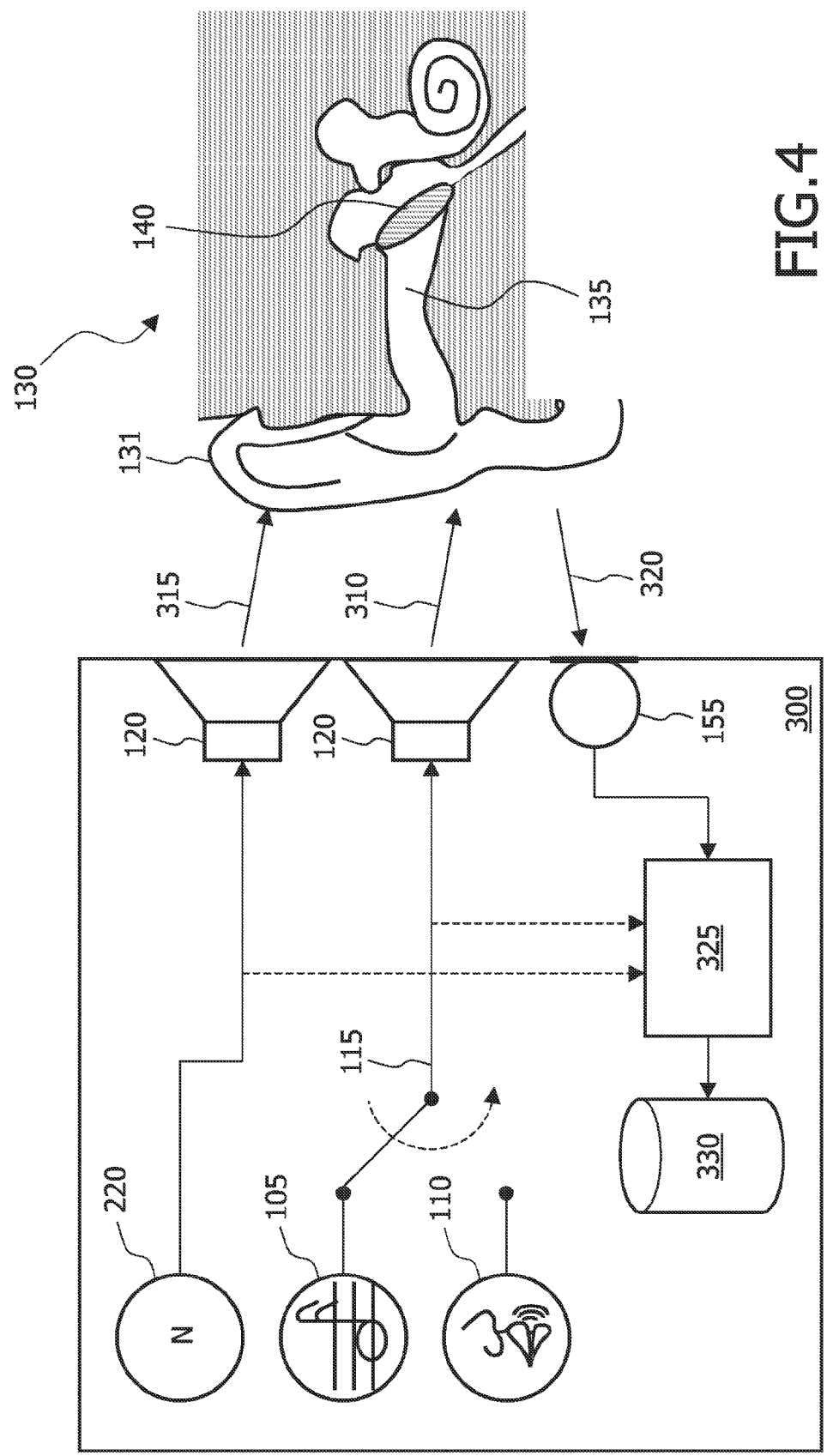
Figure 5:
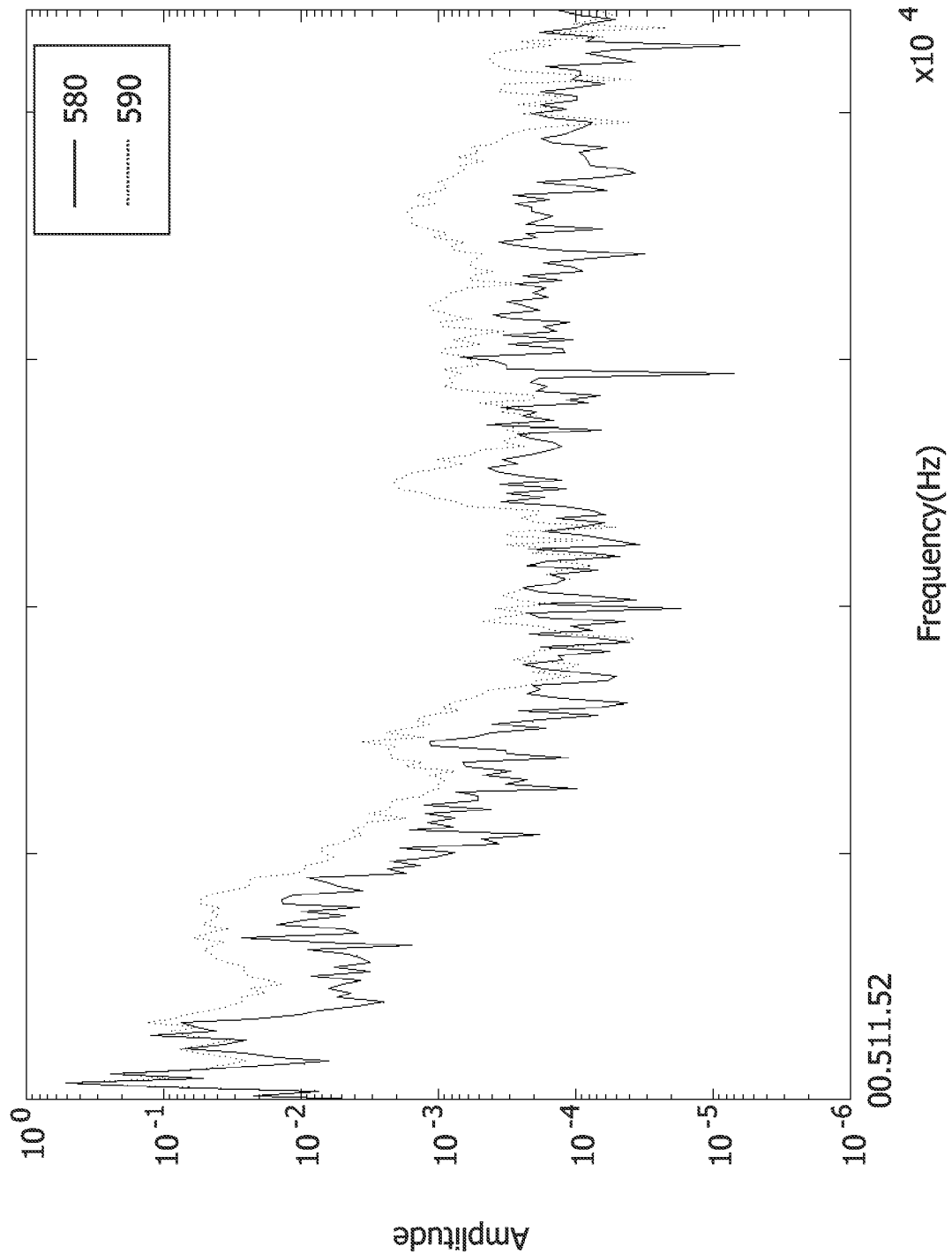
Figure 6:
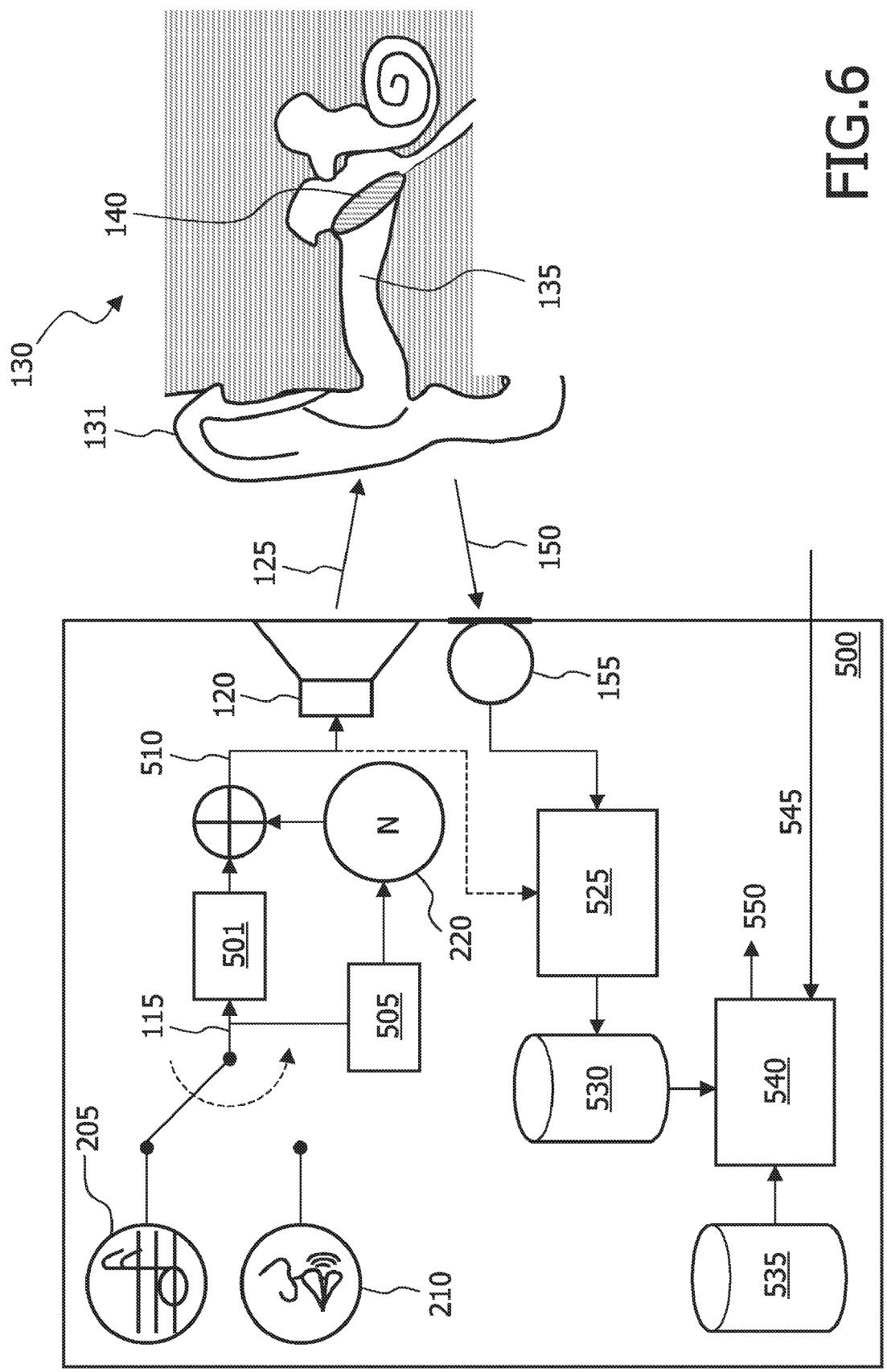
Figure 7:
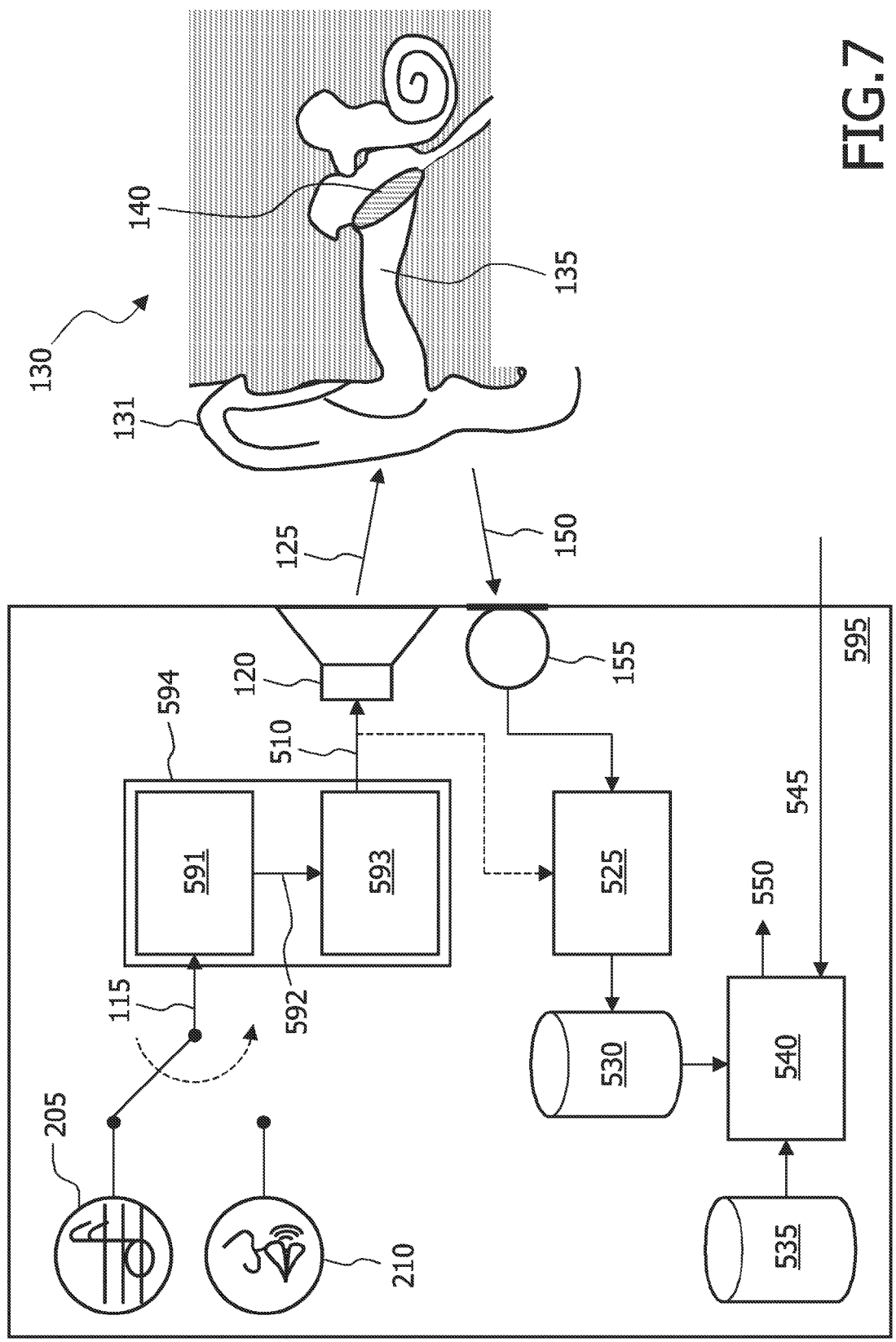
Figure 8:
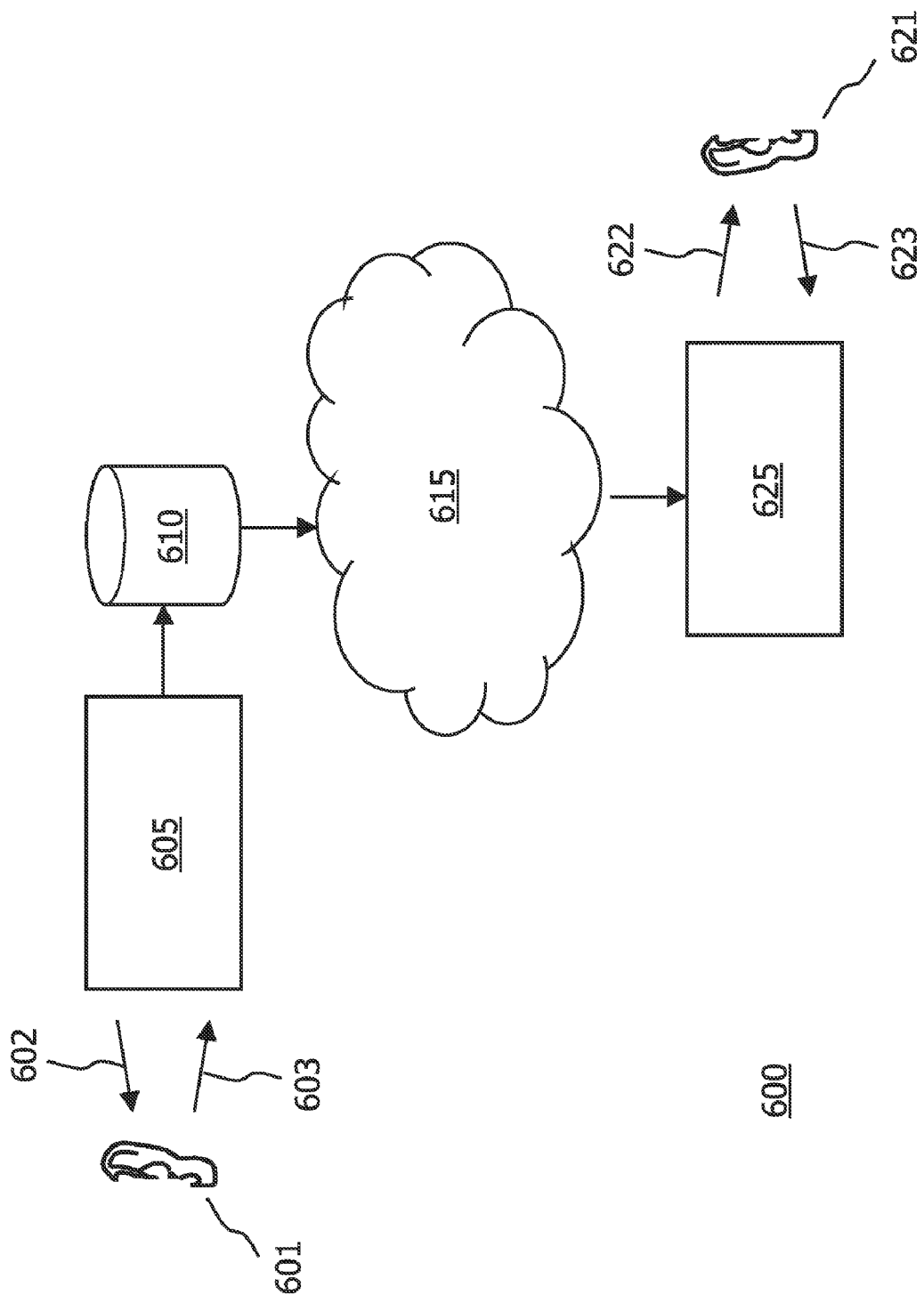
Figure 9:
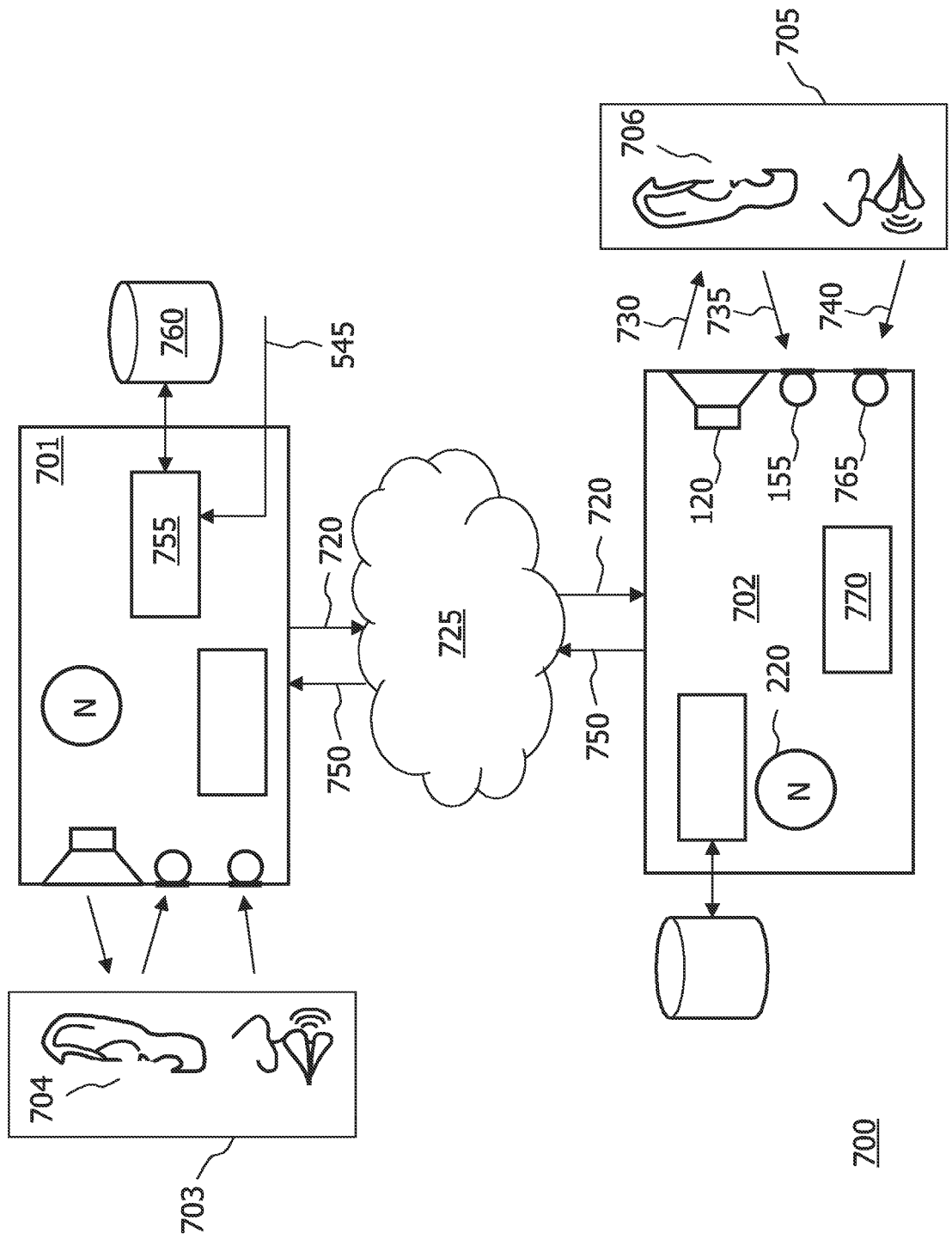

These and other aspects of the invention will be further elucidated and described by way of example and with reference to the drawings, in which:

FIG. 1 is a schematic representation of an apparatus according to the first aspect of the present invention for characterizing a human outer ear, FIG. 2 is a plot depicting the amplitude of the "ear transfer function" over frequency characterized according to the present invention, for three individuals, FIG. 3 is a schematic representation of an apparatus according to the second aspect of the present invention for characterizing a human outer ear, FIG. 4 is a schematic representation of an alternative apparatus according to the second aspect of the present invention for characterizing a human outer ear, FIG. 5 is a plot depicting the amplitude of the "ear transfer function" over frequency characterized according to the present invention, with and without added noise, FIG. 6 is a schematic representation of an apparatus for authenticating a person based on the third aspect of the present invention for characterizing a human outer ear, FIG. 7 is a schematic representation of an alternative apparatus for authenticating a person based on the third aspect of the present invention for characterizing a human outer ear, FIG. 8 is a schematic representation of a system for identifying a person based on the acoustical properties of an outer ear, FIG. 9 is a schematic representation of a system for remote authentication of a person, using a telecommunication system.

Throughout the drawings, the same reference numerals refer to the same elements, or elements that perform the same function.

Well-known biometric methods for identity verification are based on biometrics such as fingerprints, irises, faces, or speech. Here, measurements are performed in order to obtain biometric data, also known as feature vector data. As a rule, not all biometrics are suitable for all applications. Characteristics such as the price and/or form factor of the required sensors, or the effort involved in deriving characteristics/feature vectors from sensor measurements, can limit the scope of application.

The acoustical properties of the outer ear, in particular the pinna (the outer flap of the ear), the ear canal, and the eardrum, can be measured with little effort, using low-cost loudspeakers and microphones. The shape of the outer ear, such as the folds of the pinna and the length and shape of the ear canal, differs among individuals, as can be observed by visual comparison of the ears of individuals. These differences are even more pronounced for acoustical measurements, and in particular for the transfer function of the outer ear when characterized, using a loudspeaker close to the ear and a microphone close to or in the ear canal.

When a pre-defined first acoustic signal is transmitted towards the outer ear of a person, the acoustic signal is in part reflected by the outer ear. In parallel, a second acoustic signal is received for characterization. Such a characterization can be used to acquire biometric data for biometric authentication/identification.

In one embodiment, characterization involves transforming the second acoustic signal into the frequency domain and comparing the resultant spectrum with previously enrolled spectra. In a different embodiment, a transfer function is established to characterize the acoustical properties of the outer ear. Such a transfer function can be established in such a way that it is independent of the first acoustic signal and, as a result, can be used to characterize an ear on the basis of different acoustic signals. To establish a transfer function during enrolment that is truly independent of the first acoustic signal, it is relevant to establish the transfer function for all relevant frequency components. Furthermore, in order to be able to reliably authenticate or identify a person, the first acoustic signal used during authentication/identification must provide sufficient information so as to differentiate between individuals.

The ear canal is a resonance system that, together with the pinna, provides rich features. In a coarse approximation, the outer ear is a one-dimensional system that resonates at one quarter of the acoustic wavelength. The resonance is typically around 2500 Hz but varies from person to person. The typical resonance frequencies correspond to typical dimensions of both pinna and ear canal.

The length of the ear canal and the curvature of the pinna have dimensions that can range from millimeters to a few centimeters. To be able to detect these shapes and curvatures, the acoustic probing waves should have proper wavelengths. Assuming that it is possible to resolve structures of the order of one tenth of the wavelength, an acoustic signal ranging from 100 Hz to 15 kHz will allow detection of feature sizes up to approximately 2 mm, which seems sufficient for distinguishing most features. Although the range from 100 Hz to 15 kHz may suffice for practical applications, it does not exclude the use of the present invention for other ranges of the audible spectrum ranging from 20 Hz to 22 kHz.

When a fixed pre-determined signal is used as a first acoustic signal during enrolment and identification/authentication, it may suffice to compare the frequency spectrum of the resultant second acoustic signal in order to authenticate and/or identify individuals. To be able to differentiate between different individuals, the first acoustic signal must have sufficient characteristic features available. Generally, the first acoustic signal does not need to have a flat spectrum in which all frequency components are present to allow successful characterization for authentication/identification.

However, when characterizing a transfer function in order to obtain an input-independent transfer function, all frequency components are relevant. In order to obtain an accurate transfer function, all frequency components must be present. In particular in music and or speech, in which generally not all spectral components are present, noise can be added to complement the spectrum. In this way, the resultant outer ear transfer function can be characterized for all relevant frequency components in the range of 100 Hz to 15 kHz, rather than for a subset. As a result, the transfer function can also be used in combination with other excitation signals.

FIG. 1 depicts an apparatus 100 according to the present invention for characterizing the acoustical characteristics of an outer ear. The apparatus comprises a storage means, such as a hard disk, for storing a digital representation of music 105 and speech 110. Either representation can be used to measure the response, although typically music will have a somewhat broader frequency spectrum than speech.

One of the representations is selected as the source signal 115. The apparatus 100 uses the source signal to generate a first acoustic signal 125. To this end, the apparatus 100 comprises a loudspeaker 120 positioned preferably in the proximity of the ear. The loudspeaker 120 transmits the first acoustic signal 125 towards the outer ear 130, comprising pinna 131, ear canal 135, and eardrum 140. Parts of the first acoustic signal 125 are reflected by the outer ear 130, and a resulting second acoustic signal 150 is received by a microphone 155 fitted close to or in the ear canal 135. The second acoustic signal 150 may also comprise environmental noise that can be measured separately by using a further microphone (not shown), and can be subsequently weighted and subtracted from the output of the microphone 155.

In the embodiment shown in FIG. 1, the characterizing means 160 uses both the selected source signal 115 as well as the microphone output 170 to establish a transfer function characterizing the outer ear 130.

In order to establish this transfer function, the characterizing means 160 transforms the source signal 115, x(t), into a frequency domain representation $X(\omega)$, using a Fast Fourier Transform (FFT). Use of other time domain-to-frequency domain transformations, including Discrete Fourier Transforms can also be envisaged. The microphone output 170, r(t), is also transformed, resulting in $R(\omega)$. Subsequently, a transfer function is established:

$$H(\omega) = R(\omega)/X(\omega)$$

This transfer function is an approximation of the actual transfer function and can be represented as a cascade of:
the transfer function of the loudspeaker ($H_{lsp}(\omega)$),
the transfer function of the outer ear ($H_{ear}(\omega)$),
the transfer function of the microphone ($H_{mic}(\omega)$).

$$H(\omega) = H_{lsp}(\omega) \cdot H_{ear}(\omega) \cdot H_{mic}(\omega)$$

Although this transfer function also includes the transfer functions of both loudspeaker 120 and microphone 155, these can be chosen within predefined specifications leaving the transfer function of the ear as the characteristic part.

The resulting transfer function ($H(\omega)$) is a complex entity. In a preferred embodiment, the characterizing means 160 discards delay and phase shift information and uses the amplitude of the transfer function as acoustical properties 165. The delay and phase shift information, and thereby some differentiating information, will be lost by using the amplitude of the transfer function. However, it is expected that this will result in a gain of robustness by reducing intra-class variation. The acoustical properties 165 can be used as a biometric feature vector in a method of authentication and identification.

Although the apparatus depicted in FIG. 1 comprises both the loudspeaker 120 and the microphone 155, it is possible to partition the apparatus into two modules that can be separated during use, for example, an apparatus comprising a first module in the form of a wireless headset comprising both the loudspeaker 120 and the microphone 144, and a second module comprising a handheld device wherein the two modules are arranged to communicate with each other by means of a wireless communication protocol such as Bluetooth using wireless communication means.

FIG. 2 depicts a set of transfer functions $|H(\omega)|$ 180, 185, 190, as established for three individuals characterized by using one piece of music. FIG. 2 is illustrative of the wealth of features present in the transfer functions. Each transfer function 180, 185, 190 shows characteristic peaks where a particular transfer function differs considerably from the other transfer functions, thereby providing sufficient opportunity to differentiate between these three persons.

FIG. 3 depicts an apparatus 200 according to the second aspect of the present invention for characterizing a human outer ear 130.

The apparatus 200 comprises a storage means, such as a memory comprising two representations of an audio signal, one comprising speech 110 and another comprising music 105. One of these representations is selected as a source signal; the selected source signal 115. The apparatus further comprises a noise generator 220, which is arranged to generate noise that can be added to the selected source signal 115. The resulting signal is a noisy selected source signal 225 that is used by the apparatus 200 to generate a first acoustic signal 125. In order to generate the first acoustic signal, the apparatus 200 comprises a loudspeaker 120.

In one embodiment, the added noise is white noise that effectively increases the background noise of the selected source signal 115 in a uniform manner. In an alternative embodiment, the noise comprises colored noise with spectral components in the range of 100 Hz to 15 kHz, which are limited, or no spectral components in the selected source signal spectrum.

In parallel with the transmission of the first acoustic signal, the microphone 155 receives a second acoustic signal 150. The microphone output 170 is sent to the characterizing means 245. The characterizing means 245 uses the microphone output 170 to characterize a transfer function which, at least in part, is based on the acoustical properties of the outer ear 130. In this embodiment, the acoustical properties are based on the noisy version of the selected source signal 225 and the output of the microphone 155.

Although it is possible to add noise to the selected audio representation 115, it is also possible to perform this addition in the analog (electric), or even in the acoustic domain. FIG. 4 depicts an apparatus 300 in which the noise generator 220 is arranged as a source for a separate loudspeaker. Here, the first acoustic signal is effectively added in the acoustic domain by superposition of the signals 315 and 310.

An apparatus for characterizing acoustical properties of an outer ear such as depicted in FIGS. 3 and 4 resembles an apparatus for enrolment of acoustical properties of an outer ear of a person. Both characterize acoustical properties. However, in the case of enrolment, it is important to do so in a reliable manner so as to facilitate a robust authentication or identification. Typically, an apparatus for enrolment of acoustical properties will perform a series of characterizations, using a series of first acoustic signals. Subsequently, the results of the characterization process will be combined in order to obtain a more reliable characterization.

FIG. 5 is a plot depicting the amplitude of two transfer functions over frequency characterized according to the present invention. The first transfer function 580 is established while using music by means of an apparatus as shown in FIG. 1, whereas the second transfer function 590 was characterized while using music with added noise by means of an apparatus as shown in FIG. 3. This plot illustrates that by enhancing the first acoustic signal, by adding noise, the resulting transfer function will also be enhanced. This particular plot shows that the transfer function is emphasized for large parts of the spectrum, and in addition is "smoothed" over the entire audible spectrum.

The inventors have found that the application of a lossy audio compression algorithm is a particularly elegant method of adding noise to a music and/or speech signal. Lossy audio compression algorithms are typically based on a psycho-acoustic model of the human auditory system. As the name suggests, lossy compression involves discarding information comprised in the original audio signal. The discarded information can also be considered as a noise signal added to the original audio content. As a result, a lossy compressed audio file, such as a file encoded by means of well-known audio compression standards such as MPEG audio layer 2 or 3, AAC, ATRAC, or WMA, may comprise large quantities of additional noise, albeit encoded in an inaudible fashion. In fact, the higher the compression ratio used during encoding, the larger the amount of additional noise. Consequently, when a lossy compressed audio signal is used for characterization, the added noise may benefit the characterization process.

Although lossy compressed audio already provides additional noise, a further improvement is possible. FIG. 6 depicts an apparatus 500 for authenticating a person by using previously enrolled acoustical properties. The apparatus 500 comprises various components also found in FIG. 3. The apparatus 500 further comprises a noise generator control means 505 that analyzes the selected representation 115, and, based on a psycho-acoustic model of the human auditory system, determines the amount of noise that can be added, as well as the frequency band in which it has to be added to the selected representation 115 without causing audible distortions in the first acoustic signal 125.

Apparatus 500 uses the same psycho-acoustic model of the human auditory system as is used in lossy digital audio compression, but the goal is different. The goal of a system applying lossy digital audio compression is to efficiently use a constrained number of bits to encode the audio signal while minimizing the perceived distortion. As a result, the lossy audio compression algorithm will focus on the reduction of the number of frequency components that need to be encoded.

In contrast, the present invention aims to add as much noise as possible to the first acoustic signal in order to optimize detection while minimizing the perceived distortion. A method according to the present invention does not have the bit-rate constraint found in a lossy audio compression algorithm. As a result, the present invention has more freedom to add noise to the selected source signal. For example, it is typically advantageous for a method according to the present invention to add frequency components to the selected source signal where there are none present. In contrast, such an addition would clash with the bit-rate constraint in a lossy audio compression algorithm. The present invention can exploit this additional freedom and optimize detection in an even more efficient fashion than a lossy audio compression algorithm can.

The apparatus 500 comprises a delay line 501 to allow temporal analysis of the selected representation 115 by the noise generator control means 505. The noise generator control means 505 sends a control signal to the noise generator 220 in order to control both amplitude and frequency characteristics of the noise generator output. In doing so, apparatus 500 can add noise in a hardly perceptible manner, exploiting both temporal and spectral masking. The noise generated by the noise generator 220 is added to the delayed selected representation.

The apparatus 500 uses the resultant noisy audio representation 510 to generate a first acoustic signal 125 sent to the outer ear 130 by means of a loudspeaker 120. In parallel, a second acoustic signal 150 is acquired by means of a microphone 155. The microphone output is sent to a characterizing means 525. The characterizing means 525 establishes a transfer function based on the noisy audio representation 510 and the output from the microphone 155. This transfer function can be used as, or in an alternative embodiment as a basis for, a feature vector 530. The resulting feature vector 530 is subsequently offered to the authentication means 540.

The authentication means 540 uses an alleged identity 545, for example, entered by the person being authenticated, using a keyboard, or read from a badge reader. The alleged identity 545 is used to retrieve enrolled acoustical properties from a database 535 of enrolled acoustical properties. The retrieved acoustical properties are subsequently matched with those of the resulting feature vector 530. Provided a sufficient match is found within a pre-determined range, the authentication is said to be successful. It should be noted that an authentication decision may be either a hard decision or a soft decision. The use of soft decisions is particularly beneficial in multi-modal biometric authentication systems.

To further improve the performance of the authentication system, well-known techniques such as Fischer Linear Discriminant Analysis (LDA) can be applied to characterize the most differentiating frequency components. To improve performance in a system applying Fischer LDA, the system for authenticating or identifying a person can emphasize those spectral components in the first acoustic signal that result in the most differentiating frequency components. Subsequently, the noise control generator means 505 will have to be configured so as to add as much signal energy as possible to these particular frequency components in the first acoustic signal that result in the most differentiating frequency components.

The apparatus 500 depicted in FIG. 6 represents an apparatus for biometric authentication, whose general structure is not unlike that of an apparatus for biometric identification. However, there is one main difference between these devices. In an apparatus for identification, a biometric is characterized and matched with, potentially, all entries in the reference database. In contrast, an apparatus for authentication typically only matches the established feature vector with the reference data associated with the alleged identity.

Although the use of lossy audio compression in a characterization method may not result in optimal characterization, it does present a substantial improvement over a system that does not apply noise insertion. FIG. 7 depicts an alternative apparatus 595 for authenticating a person, using previously enrolled acoustical properties. In the apparatus 595, the delay line 501, the noise generator control means 505, the noise generator 220, and the adder found in apparatus 500 (FIG. 6) have been replaced by alternative means that perform a similar function.

In the apparatus 595, the selected source signal 115 is sent to a lossy audio compression encoder 591. This encoder comprises a processor executing a lossy audio compression algorithm, or parts of such an algorithm as described below. The lossy compressed audio signal 592, output by the lossy audio compression encoder 591, is sent to a lossy audio compression decoder 593. The decoder 593 comprises a processor for executing the accompanying audio decompression algorithm, or parts thereof. The combination of both the lossy encoding and subsequent decoding results in a noisy audio representation 510 with minimal audible distortion.

A typical lossy audio compression encoder comprises three stages:
1. A Transformation Stage
   The input signal is transformed.
2. A Quantization Stage
   Signal analysis and quantization are handled in this stage. As a result, this stage is the primary cause of the loss of information (added noise).
3. An Encoding Stage
   Conventional entropy encoding techniques are used to generate a more concise representation of the quantized data.

The accompanying lossy audio compression decoder typically comprises stages that effectively mirror the encoder stages:
1. A Decoding Stage The encoded data is decoded by using conventional entropy decoding techniques.
2. A Reconstruction Stage
   An approximation of the transformed representation is reconstructed by means of the decoded data.
3. A Transformation Stage
   The transformed representation is transformed back into a signal resembling the original input signal.

In the present embodiment, the encoder and the decoder are placed back-to-back. This allows further optimization of the encoder and decoder. One important optimization is the removal of the encoding and decoding stages. Further optimizations are possible, depending on the actual algorithm applied. The resultant audio processing module 594 will perform the same function but will do so in a more efficient manner.

FIG. 8 depicts a system 600 according to the present invention. The system comprises an apparatus 605 for enrolment of acoustical properties of a person's outer ear. The apparatus 605 is used to characterize the acoustical properties of an outer ear 601, using a first acoustic signal 602 comprising music and/or speech. The apparatus 605 receives a second acoustic signal 603 and uses this to characterize acoustical properties related to the outer ear 601 that are subsequently stored in a database 610.

The system further includes an apparatus 625 for identification of a person, using acoustical properties of an outer ear. When a person is present at the apparatus 625 that needs to be identified, the apparatus 625 supplies a first acoustic signal 622 comprising music and/or speech. The first acoustic signal 622 is transmitted towards the outer ear 621 of the person being identified. The apparatus 625 receives a second signal 623 and uses this to characterize acoustical properties of the outer ear 621. The characterized acoustical properties are subsequently matched with enrolled acoustical properties from the database 610. When the difference is within a predetermined threshold, a match is found and the identity is established as being the identity associated with the database entry.

To match acoustical properties, data is sent from the database 610 to the apparatus 625 via a network 615. This network may be a GSM network, a UMTS network, a wireless LAN, a proprietary network, or even the Internet. To prevent excessive data transfers, the database may be distributed, or alternatively, the matching process may be centralized at one or multiple sites in the network.

Although the apparatus 605 and the apparatus 625 may be dedicated devices, the present invention can also be incorporated in existing or future consumer electronics devices such as mobile phones, DECT phones, regular phones, or other devices such as portable audio and/or video players that comprise earphones, or headphones.

FIG. 9 depicts a telecommunication system 700 configured to provide telecommunication services via a network and allow remote authentication of a person, using acoustical properties of an outer ear. The depicted system comprises at least two terminals; the first terminal 701 is the terminal that performs the actual authentication, the second terminal 702 in turn establishes the acoustical properties of the person 705 who is being authenticated. Although the depicted first terminal 701 is structurally similar to the second terminal 702, this is not necessary. In an alternative embodiment, the first terminal 701 may be e.g. a computer system operated by a service provider arranged to automatically answer orders placed by telephone.

The actual authentication process is distributed through both terminals. The first terminal 701 provides a representation 720 of an audio signal comprising music and/or speech. This representation 720 can be pre-recorded or created on-the-fly by the first terminal 701, e.g. by sampling the voice of the operator 703 of the first terminal 701. The representation 720 is subsequently transmitted to the second terminal 702 via a network 725. In the second terminal, noise is added to the incoming signal according to the present invention. This noisy representation is converted into a first acoustic signal 730 by the second terminal 702, using a loudspeaker 120.

The second terminal 702 further receives a second acoustic signal 735. The second acoustic signal 735 comprises reflected parts of the first acoustic signal 730. These parts are reflected by an outer ear 706 of the person 705 operating the second terminal 702. The signal registered by the microphone 155 is used together with the noisy representation in the characterizing means 770 to derive characterized acoustical properties 750. The characterized acoustical properties 750 are transmitted to the first terminal 701 via the network 725.

The first terminal 701 comprises an authentication means 755. The authentication means 755 obtains an alleged identity 545. The alleged identity 545 may be e.g. communicated by the person being authenticated to the first terminal, or may be obtained by using a card reader. Using the alleged identity 545, the authentication means obtains enrolled acoustical properties associated with the alleged identity 545 from the database 760. Subsequently, the authentication means 755 matches the characterized acoustical properties 750 with these enrolled acoustical properties. The person operating the second terminal 702 is authenticated when a sufficient match is found with the enrolled acoustical properties associated with the alleged identity 545, otherwise authentication fails.

The network used in system 725 may be a GPS network, a UMTS network, a 802.11 wireless LAN, a proprietary network, or a TCP/IP network. The system 700 can be used to remotely authenticate persons, e.g. to grant them access to services on a network, to content available through the network, or it may be used to authorize transactions, e.g. in order to allow electronic banking.

Although the system 700 depicted in FIG. 9 is partitioned in an efficient manner, it is possible to distribute functionality from the second terminal 702 to the first terminal 701. This is relevant when there is limited control of the integrity of the second terminal 702. In this scenario, it is interesting to move the characterizing means from the second terminal 702 to the first terminal 701. However, although certain networks such as a TCP/IP network allow transparent data transmission, other networks such as GSM networks may not be transparent for audio signals. As a result, re-distribution of functionality may not always be feasible.

Apart from the above-mentioned embodiments, the present invention can also be applied in consumer electronics devices such as audio and/or video playback devices utilizing headphones, or earphones. Here, the present invention can be used to identify a user and customize e.g. equalizer settings, or program offers based on the user identity.

Alternatively, a mobile phone, or an alternative device comprising earphones or headphones may be assigned exclusively to one or more particular users. In doing so, the present invention would allow an efficient theft-deterrent/abuse-prevention system for said consumer electronics device.

The present invention can allow the authentication of users with or without knowledge of said users, e.g. for allowing automatic priority scheduling in a telephone queue.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim. Use of the verb "comprise" and its conjugations does not exclude the presence of elements or steps other than those stated in a claim. Use of the article "a" or "an" preceding an element or step does not exclude the presence of a plurality of such elements or steps.

The invention can be implemented by means of hardware comprising several distinct elements, and by means of a suitably programmed computer. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method of characterizing acoustical properties of an outer ear, the method comprising:
    transmitting a first acoustic signal towards the outer ear, the first acoustic signal comprising at least one of music and speech,
    receiving a second acoustic signal from the outer ear,
    characterizing acoustical properties of the outer ear on the basis of the second acoustic signal; and
    adding spectral components to the at least one of music and speech to form the first acoustic signal so as to complement the audible spectrum of the at least one of music and speech.

2. The method of claim 1, wherein the method further comprises transmitting an acoustic noise signal towards the outer ear.

3. The method of claim 1, wherein the first acoustic signal is based on a representation of an audio signal, the representation comprising one of the following:
    an electromagnetic representation of an audio signal,
    an optical representation of an audio signal,
    an electrical representation of an audio signal, and
    a digital representation of an audio signal.

4. The method of claim 3, wherein the digital representation is a lossy compressed audio signal.

5. The method of claim 3, wherein the method further comprises processing the representation of the audio signal before converting the representation into an acoustic signal.

6. The method of claim 5, wherein the processing comprises the addition of noise to the representation of the audio signal.

7. The method of claim 5, wherein the processing comprises the addition of noise to the representation of the audio signal, the noise formed using a psycho-acoustic model of the human auditory system in order to reduce perceptual disturbance as a result of the added noise.

8. The method of claim 1, wherein the characterizing the acoustical properties of the outer ear involves a frequency domain analysis of the second acoustic signal.

9. The method of claim 8, wherein the characterizing the acoustical properties of the outer ear involves characterizing a transfer function of the acoustical properties of the outer ear.

10. The method of claim 1, further comprising enrolling the acoustical properties of an outer ear of a person being the object of the characterizing.

11. The method of claim 10, further comprising authenticating a person using previously enrolled acoustical properties of an outer ear.

12. The method of claim 10, further comprising identifying a person using previously enrolled acoustical properties of an outer ear.

13. An apparatus for characterizing acoustical properties of an outer ear, the apparatus comprising:
    a transmitter for transmitting a first acoustic signal towards the outer ear, the first acoustic signal comprising at least one of music and speech,
    an encoder for adding spectral components to the at least one of music and speech to form the first acoustic signal so as to complement the audible spectrum of the at least one of music and speech,
    a receiver for receiving a second acoustic signal from the outer ear, and
    a signal processor for characterizing the acoustical properties of the outer ear on the basis of the second acoustic signal.

14. The apparatus for enrolment of acoustical properties of an outer ear of a person, incorporating the apparatus of claim 13 for characterizing the acoustical properties of the outer ear of the person being enrolled.

15. An apparatus for authenticating or identifying a person, using previously enrolled acoustical properties of an outer ear, incorporating the apparatus of claim 13 for characterizing the acoustical properties of the outer ear of the person being authenticated.

16. The apparatus of claim 13, further comprising two modules that can be separated, wherein a first module comprises:
    the transmitter,
    the receiver, and
    a first communication device for communicating with a second module, and wherein the first module can be separated from the second module, the second module comprising:

the signal processor, and a second communication device for communicating with the first module.

17. A telecommunication system configured to provide telecommunication services via a network, the network comprising:

a first terminal, associated with a party, comprising an authenticator, a second terminal operated by a person, and both terminals connected by a network, wherein the first terminal and the second terminal characterize the acoustical properties of the outer ear of the person by transmitting a first acoustic signal towards the outer ear, the first acoustic signal comprising at least one of music and speech, receiving a second acoustic signal from the outer ear, characterizing acoustical properties of the outer ear on the basis of the second acoustic signal; and adding spectral components to the at least one of music and speech to form the first acoustic signal so as to complement the audible spectrum of the at least one of music and speech, and wherein the authenticator in the first terminal remotely authenticates the person, using the characterized acoustical properties, an alleged identity, and a database comprising enrolled acoustical properties.

* * * * *